United States Patent
Jordan et al.

(10) Patent No.: US 9,814,385 B2
(45) Date of Patent: Nov. 14, 2017

(54) OPHTHALMOSCOPE

(71) Applicants: London School of Hygiene and Tropical Medicine, London (GB); The Greater Glasgow Health Board, Glasgow (GB); The University Court of the University of St Andrews, Fife (GB)

(72) Inventors: Stewart Jordan, Naturu (KE); Mario Giardini, Fife (GB); Iain Livingstone, Glasgow (GB); Andrew Bastawrous, London (GB)

(73) Assignees: London School of Hygiene and Tropical Medicine, London (GB); The Greater Glasgow Health Board, Glasgow (GB); The University Court of the University of St Andrews, Fife (GB)

( * ) Notice: Subject to any disclaimer, the term of this patent is extended or adjusted under 35 U.S.C. 154(b) by 87 days.

(21) Appl. No.: 14/889,730

(22) PCT Filed: May 2, 2014

(86) PCT No.: PCT/GB2014/051372
§ 371 (c)(1),
(2) Date: Nov. 6, 2015

(87) PCT Pub. No.: WO2014/181096
PCT Pub. Date: Nov. 13, 2014

(65) Prior Publication Data
US 2016/0120404 A1    May 5, 2016

(30) Foreign Application Priority Data
May 7, 2013 (GB) .................................. 1308131.0

(51) Int. Cl.
*A61B 3/10* (2006.01)
*A61B 3/14* (2006.01)
(Continued)

(52) U.S. Cl.
CPC ............... *A61B 3/14* (2013.01); *A61B 3/0008* (2013.01); *A61B 3/0025* (2013.01); *A61B 3/12* (2013.01);
(Continued)

(58) Field of Classification Search
CPC ......... A61B 3/0008; A61B 3/11; A61B 3/112; A61B 3/14; A61B 3/15; A61B 3/156; A61B 3/158
(Continued)

(56) References Cited

U.S. PATENT DOCUMENTS 7,905,598 B2 *    3/2011    Kishida ................ A61B 3/1241
                                                       351/206
2011/0085138 A1    4/2011    Filar
(Continued)

FOREIGN PATENT DOCUMENTS

CN    102334976    2/2012
DE       323161    *  7/1920    ............. A61B 3/156
(Continued)

OTHER PUBLICATIONS

Bastawrous et al., "iPhones for eye surgeons," *Eye*, vol. 26, No. 3, pp. 343-354, 2012.
(Continued)

*Primary Examiner* — Huy K Mai
(74) *Attorney, Agent, or Firm* — Klarquist Sparkman, LLP

(57) ABSTRACT

The invention relates to an ophthalmoscope comprising a camera and an associated illumination device; the invention further concerns a novel method for processing a plurality of
(Continued)

images of the eye taken by said device; and software, typically included in said ophthalmoscope, for executing said method.

14 Claims, 7 Drawing Sheets

(51) Int. Cl.
*A61B 3/00* (2006.01)
*G06T 3/40* (2006.01)
*A61B 3/12* (2006.01)

(52) U.S. Cl.
CPC ............ *G06T 3/4053* (2013.01); *A61B 3/145* (2013.01); *A61B 2576/02* (2013.01)

(58) Field of Classification Search
USPC .......................... 351/206, 211, 213–216, 221
See application file for complete search history.

(56) References Cited

U.S. PATENT DOCUMENTS

| | | |
|---|---|---|
| 2011/0176109 A1 | 7/2011 | Mann |
| 2011/0279776 A1 | 11/2011 | Spaide |
| 2013/0083185 A1* | 4/2013 | Coleman, III ........... A61B 3/14 348/78 |
| 2014/0198298 A1* | 7/2014 | Cheng ...................... A61B 3/14 351/206 |

FOREIGN PATENT DOCUMENTS

| | | | |
|---|---|---|---|
| EP | 2 609 853 | 7/2013 | |
| WO | WO 2004/017825 | 3/2004 | |
| WO | WO 2004/082465 | 9/2004 | |
| WO | WO 2011/047214 | 4/2011 | |
| WO | WO 2012/026597 | 3/2012 | |
| WO | WO2012/039998 A1 * | 3/2012 | ............... A61B 3/14 |
| WO | WO 2012/177544 | 12/2012 | |
| WO | WO 2013/049778 | 4/2013 | |
| WO | WO 2013/071153 | 5/2013 | |
| WO | WO 2014/074250 | 5/2014 | |

OTHER PUBLICATIONS

Bastawrous et al., Validation of near eye tool for refractive assessment (NETRA)—pilot study, *Journal of Mobile Technology in Medicine*, vol. 1, No. 3, pp. 6-16, 2012.
International Search Report and Written Opinion issued by European Patent Office dated Sep. 8, 2014, for PCT/GB2014/051372, 17pp.
Prasanna et al., "Decision support system for detection of diabetic retinopathy using smartphones," 2013 Seventh International Conference on Pervasive Computing Technologies for Healthcare (Pervasive Health), pp. 176-179, 2013.
Search Report under Section 17(5) issued by Intellectual Property Office dated Nov. 4, 2013 for GB1308131.0, 6pp.
Scheffer et al., "Biomedical engineering education through global engineering teams," Engineering in Medicine and Biology Society 2012 International Conference of the IEEE, pp. 5058-5061, 2012.
Tahiri et al., "Les smartphones en ophtalmologie," *Journal Francais d'ophtalmologie*, vol. 36, No. 6, pp. 499-525, 2013 (abstract only).

* cited by examiner

Figure 1 – Illuminator principle 1
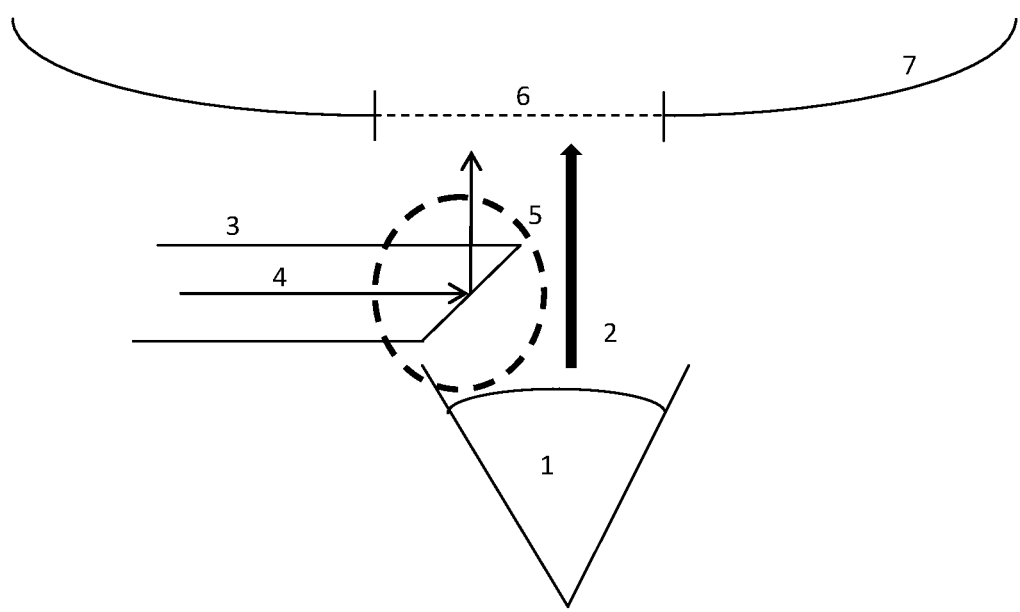

Figure 2 – Illuminator principle 2
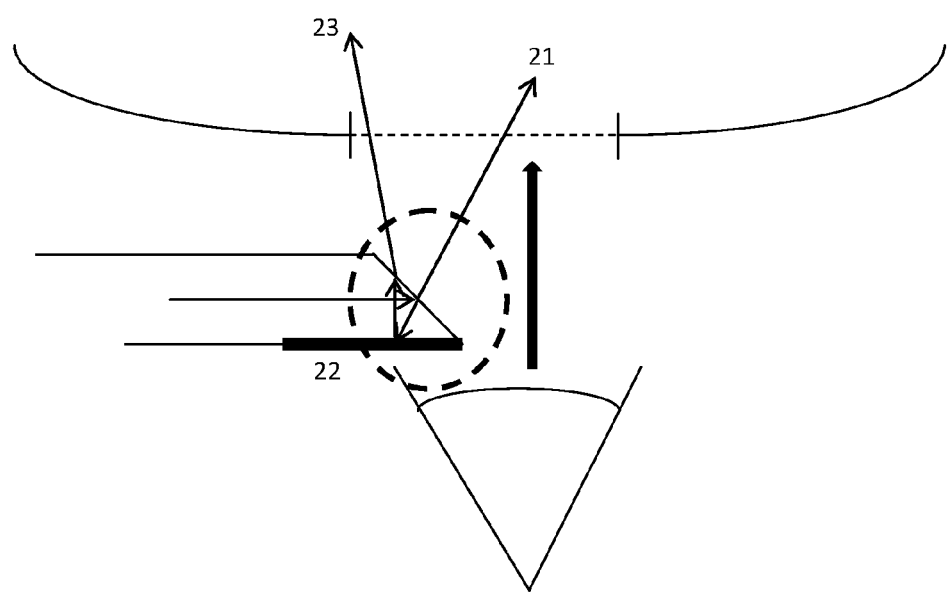

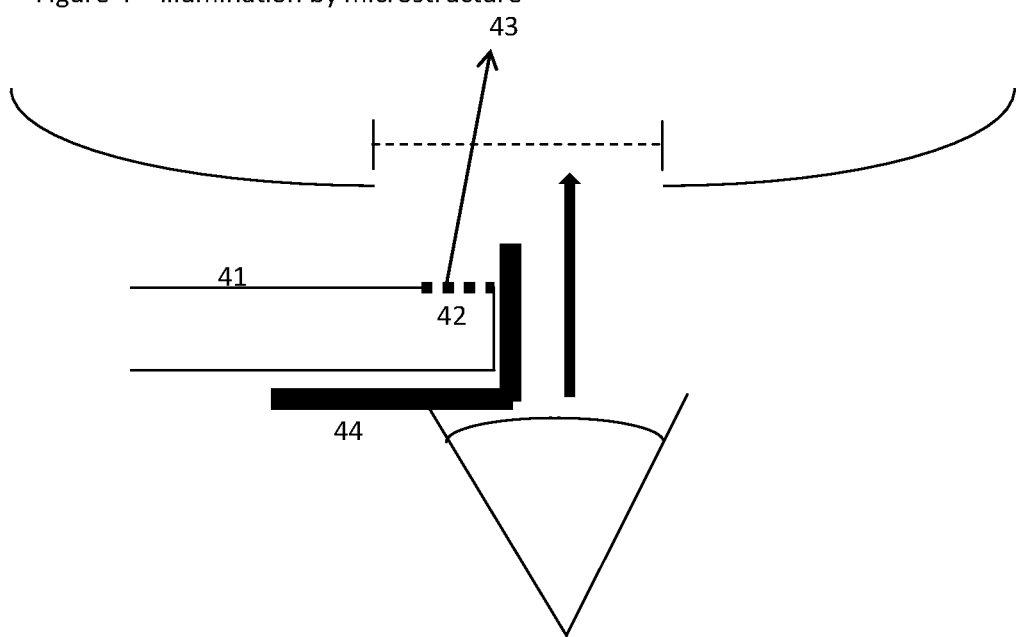
Figure 4 – Illumination by microstructure

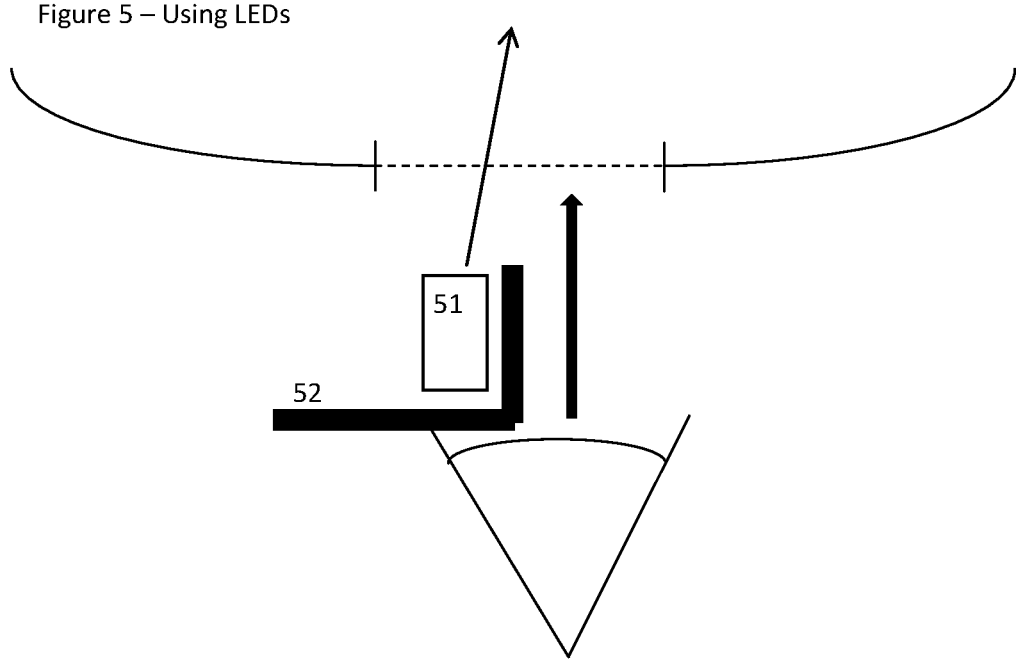

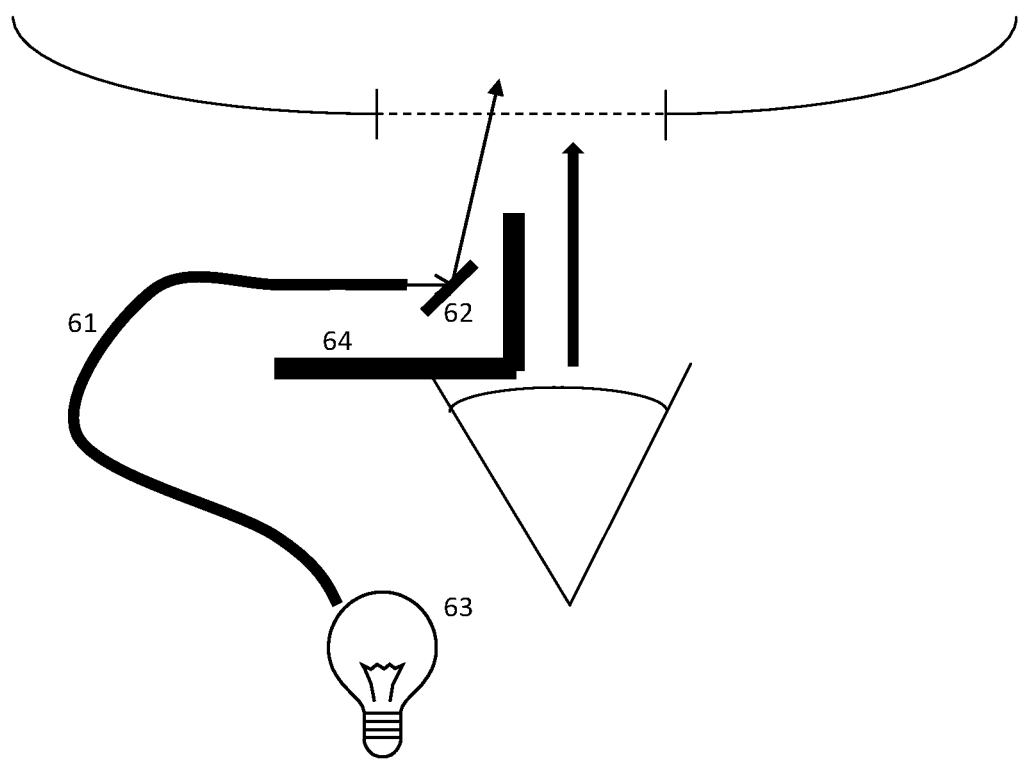
Figure 6 – Using optical a fibre or a fibre bundle

Figure 7 – avoiding reflections
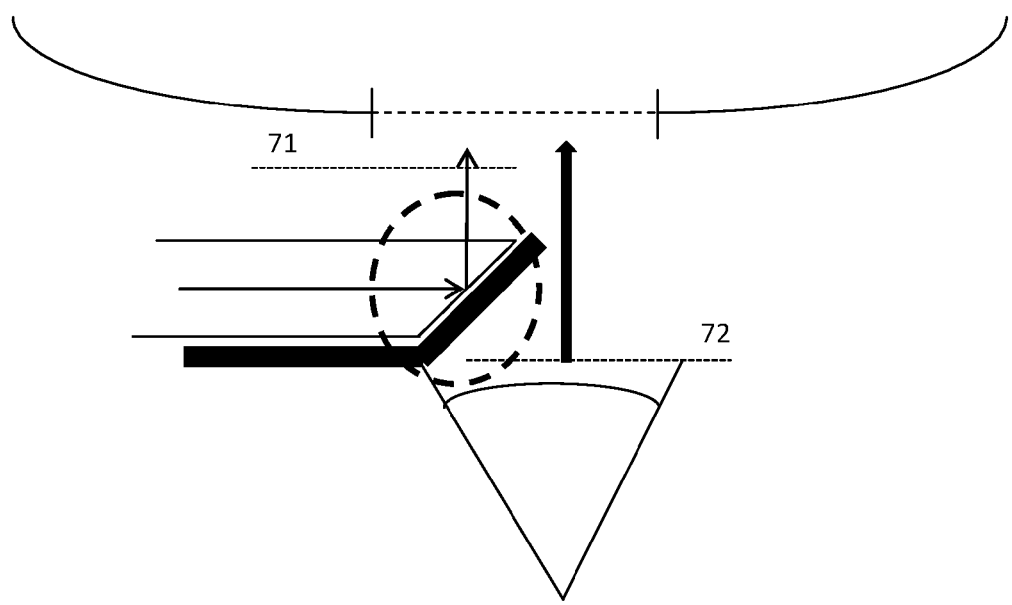

OPHTHALMOSCOPE

CROSS REFERENCE TO RELATED APPLICATIONS

This is the U.S. National Stage of International Application No. PCT/GB2014/051372, filed May 2, 2014, which was published in English under PCT Article 21(2), which in turn claims the benefit of Great Britain Application No. 1308131.0, filed May 7, 2013. The provisional application is incorporated herein in its entirety.

FIELD OF THE INVENTION

The invention relates to an ophthalmoscope comprising a camera and an associated illumination device; the invention further concerns a novel method for processing a plurality of images of the eye taken by said device; and software, typically included in said ophthalmoscope, for executing said method.

BACKGROUND OF THE INVENTION

In 2004 the World Health Organisation reported the top five causes of visual impairment (VI) and blindness worldwide as (1) Cataract, (2) Glaucoma, (3) Age Related Macular Degeneration (AMD), (4) Corneal opacities and (5) Diabetic Retinopathy (DR). Globally, the number of people of all ages with VI is 285 million. The initiative Vision 2020 has largely focussed on the elimination of cataract due to its amenability to cure through surgery.

Approximately 80% of blindness is preventable or curable. The majority (90%) of those blind worldwide live in low-income countries. Human and technological resources for the provision of eye care follows the Inverse Care Law, i.e. where the majority of the blind people live, are the least existing resources, and conversely; in areas of low blindness, high provision of resources exist. To create sustainable health services, accurate and representative data needs to be collected about VI so that policy makers can distribute limited resources in a manner that maximizes patient benefit and also so that planning for future requirements and infrastructure can be determined.

In low-income countries there are insufficiently trained personnel and a lack of ophthalmic equipment for the detection of potentially blinding conditions. This means many people do not receive the necessary eye treatment and so are left with vision impairment.

Cost is the main hurdle to providing the ophthalmic equipment in these settings, because the equipment is large, complex and costly. Moreover, even if ophthalmic equipment is available there are often logistical constraints associated with transporting this equipment across large distances in what is often environmentally hostile terrain. The training of specialised personnel is also costly and even when trained there are often not enough specialists available to cover the area or population to be screened.

Global loss in productivity as a result of VI is thought to be 121 billion US$, thus there is an invidious spiralling decline in healthcare as VI increases. Given that 80% of blindness is preventable or curable if detected early enough, it follows that a sensible eye care strategy can positively affect not only the wellbeing of each individual but also a population or country as a whole increasing not only health but GDP and so the ability to yet further improve healthcare.

In the developed world, whilst eye care is available, especially for individuals who are able to visit an opticians or an ophthalmologist, it is costly and with an expanding population there is an ever increasing desire to undertake healthcare in the most efficient and effective way possible. Thus there is also a need within the developed world to improve healthcare so that more individuals can be effectively treated per unit investment.

Moreover, there is also a need to be able to take healthcare into various communities such as schools, retirement homes, and prisons, the prerequisite for which is the development of portable devices which are easy to use by trained but not necessarily experienced or senior staff.

In the medical examination of the eye, the visualisation of the retina through the pupil (ophthalmoscopy) is performed on a routine basis. This is done, in routine testing, through an instrument called a "direct ophthalmoscope". It is a pen-sized (approximately 20 cm) viewing system held by a doctor in front of the patient's eye, often at very close face-to-face distance. Such an instrument is simple, relatively inexpensive, yet rather difficult to use. In the western world, training is typically undertaken at undergraduate level within optometry and medicine. The field of view is very small (5 degrees at best), the aiming is critical and the focussing requires great manual dexterity. Moreover, the segmentation of the image in to very small fields requires the operator to look at a small portion of the retina at a time, and to reconstruct a "mental image" of the retina itself.

To overcome these limitations, a more expensive instrument can be used. It is called an "indirect ophthalmoscope". It consists of a short-focal-length lens (known in the practice as "superfield"), which the doctor holds in front of the patient's eye, and a headpiece, which carries a viewer that projects light through the lens, or superfield, into the eye. The user aligns by hand the lens, the eye and the viewer, and looks at the retina. The field of view is much wider than a direct ophthalmoscope (40 degrees). However, the system is expensive and the use can be difficult due to the intrinsically delicate manual alignment. Proficiency in this technique is typically limited to post-graduate ophthalmology sub-specialist doctors.

Two further instruments are derived from the indirect ophthalmoscope: a fundus camera and a panoptic ophthalmoscope. In the "fundus camera", an indirect ophthalmoscope is pre-aligned. The patient's head is immobilised through a head-and-chin rest, and a photograph is taken through the pre-aligned, indirect ophthalmoscope using a camera. The panoptic ophthalmoscope is a proprietary instrument. This indirect ophthalmoscope is pre-aligned, and held by a doctor as a single unit in front of the patient's eye. The user observes the retina through the instrument. A camera can be attached to the device.

Attempts have been made to build ophthalmoscopes by using small digital cameras (e.g. webcams) either attached to an ophthalmoscope, or held directly in front of a patient's eyes, with an associated set of prisms, including refraction compensating lenses, to project light into the eye, in order to provide the necessary illumination. Unfortunately, the results have been disappointing because the size of the prisms causes either a gross reduction of the field of view or poor resolution and focus.

With the above in mind we have developed an ophthalmoscope based on an autofocussing miniature camera typically a smartphone camera. Alternatively, the camera can avoid autofocussing if the depth of field is long enough for example using a non-autofocusing, low-numerical aperture system is a way to improve the depth of focus. In other words, the system can be built to be "focus-free", such as in inexpensive webcams. Whilst the use of smartphones to test for eye disorders is not new, indeed we have suggested the use of this technology in this particular discipline in the past (Journal of Mobile Technology in Medicine [JMTM] Vol. 1 issue 3 Sep. 2012 & Eye 2012, 26, 343-354) and others have commented favourably upon the idea (Ophthalmology Volume 119, Number 10, October 2012), no one has thought to use a smartphone for direct ophthalmoscopy and no one has produced a device which is simple, effective and reliable, which can visualise the fundus without substantial training and which offers a substantial field improvement on standard direct ophthalmoscopy, bringing the specifications close to indirect ophthalmoscopes or fundus cameras.

STATEMENTS OF INVENTION

According to a first aspect of the invention, there is provided an ophthalmoscope comprising a camera and an associated illumination device whereby an eye of a patient is illuminated prior to the taking of at least one photograph of same; wherein said illumination device at least in part is placed, when in use, in front of the camera and further wherein said illumination device comprises a light channeling member for directing light into the eye to be photographed.

In a preferred embodiment of the invention said camera is an automatically-focusing camera.

In yet a preferred embodiment of the invention said channeling member also, advantageously, blocks scattered light from entering said camera.

In a further preferred embodiment of the invention said illumination device comprises a light source and said light channeling member is either a miniature prism or a miniature optical fibre attachment. Preferably, when referring to a miniature prism or a miniature optical fibre attachment the size under consideration is in the order of 1×1×5 mm up to 1×1×30 mm. This, advantageously, ensures the working distance can be as low as 1-2 mm.

In yet a further preferred embodiment of the invention said prism is provided with at least one reflective member positioned so that light exiting from said prism is reflected towards said eye. Ideally, said reflective member is located towards the rear of the prism or away from said eye. In yet a further preferred embodiment of the invention said reflective member is located on a first side of said prism and, more ideally still, on a first and a second side of said prism whereby light exiting from said prism is reflected towards said eye.

In a further preferred embodiment of the invention said optical fibre attachment is a waveguide with at least one opening positioned so that, in use, light exiting from said waveguide is directed towards said eye. More preferably, said waveguide comprises a plurality of openings and, ideally, has a scattering structure, ideally but not exclusively, made from corrugations, frosting, or the inclusion of particles. Other scattering surfaces or re-emissive surfaces (e.g. by fluorescence) will be well known to those skilled in the art and may be used in the working of the invention.

In a further preferred embodiment of the invention said waveguide is provided with at least one reflective member whereby light exiting from said waveguide is reflected towards said eye. Ideally, said reflective member is located towards the rear of the waveguide or away from said eye. In yet a further preferred embodiment of the invention said reflective member is located on a first side of said waveguide, and more ideally still, on a first and a second side of said waveguide whereby light exiting from said waveguide is directed towards said eye.

In a further preferred embodiment of the invention said channeling member therefore consists of or comprises a light source/guide and a reflective surface or, alternatively, said light source/guide is positioned adjacent a reflective surface which herein is referred to as a shield. Thus the channeling member and its shield, directs light into the eye to be photographed and prevents scattered light from entering said camera.

In yet a further preferred embodiment of the invention said illumination device comprises at least one further blocking member. Said blocking member is for blocking scattered or reflected light which would otherwise enter said camera. Most preferably, said blocking member is located in front of said light channeling member. Additionally, or alternatively, said blocking member is provided separate from said illumination device and is positioned either in front of, or rear of, said illumination device but, in either event, in front of said camera. More preferably still said blocking member comprises at least one, and ideally, a pair of polarisers whereby light directed into said eye is prevented from being reflected, refracted or directed towards said camera.

In yet a further preferred embodiment of the invention said light source is a Light-emitting diode (LED), Organic LED (OLED), a flame, a fluorescence emission, an electric discharge in a gas, a conventional lamp or sunlight/daylight.

In yet a further preferred embodiment of the invention light of one colour may be used e.g., blue or ultraviolet and the channelling member is made, at least in part, of a material emitting the desired light spectrum (e.g. white, or red-free) in this instance a suitable material would be a fluorescent material.

In one embodiment of the invention, particularly where the light source is an LED or lamp, said light channeling member takes the form of at least one reflective surface positioned at least partially about or adjacent said light source whereby light is directed into the eye to be photographed.

In yet a further preferred embodiment of the invention said camera is a webcam or a mobile phone camera, digital camera, film camera, or camera of a tablet or laptop computer.

Advantageously, where the light source is an LED, or some other electrically powered source it can, optionally, be powered by the sound output jack of the phone/computer running the camera. Typically the electrical waveform generated at the sound output is fed to the light source, after optional rectification.

According to a second aspect of the invention there is provided a method for visualising the retina through the pupil (ophthalmoscopy) of an individual involving the use of the ophthalmoscope of the invention.

In use, we take an automatic-focus small camera, such as a good webcam or a good mobile phone camera (we typically use the whole phone, without modifications). We use the autofocussing feature of the camera to compensate for viewing defects (ametropies). We inject light into the eye by using in front of the camera either an appropriate miniature prism or a miniature optical fibre attachment. We then move the camera very close to the eye, effectively using the pupil as a window onto the retina. This is the principle currently used in direct ophthalmoscopy. However, the very small size of our illuminating device as well as the small size of the front lens of the autofocussing camera, allows us to move very close to the eye itself, thus expanding the field of view. In fact, we obtain a field of view comparable to an indirect ophthalmoscope, with a resolution comparable to the best fundus cameras.

Advantageously, the image quality is superb and the ease of use is such that an untrained operator can use the instrument after only a few minutes of instructions. The instrument has the potential to replace standard, bulky indirect ophthalmoscopy, panoptic ophthalmoscopy and retinal imaging through fundus cameras within a very small amount of time. Moreover, the instrument allows untrained personnel to take images in-field (such as in developing countries, in prisons, in aerospace settings, in scientific expeditions, etc.) and to relay them easily and directly to an analysis point (hospital, ophthalmic practice), e.g. for screening, or for emergency or remote diagnostics. Moreover, with the use of appropriate software the instrument allows relatively untrained personnel to make a diagnosis using a captured image.

The ability to couple such innovative technology to a phone also allows us to take advantage of the processing capabilities of the phone itself. For example, we have developed an enhanced retinal imaging piece of software, or an 'app', which uses a plurality of images—taken as separate photographs or provided by reducing a video into separate images, aligns then reduces the images into a single high definition image and stitches multiple high definition images together to create a single wide field retinal image.

According to a further preferred embodiment of the ophthalmoscope of the invention, or a further aspect of the invention, there is therefore provided a method for obtaining an image of the eye comprising:

a) providing a plurality of images of an area to be viewed;
b) aligning said images having regard to at least one reference point; and
c) reducing the aligned images into a single high definition image.

Ideally said reference point is common to at least two images but may be common to the majority or even all the images, largely, but not exclusively, depending upon whether the images represent a panoramic view or multiple images of a smaller field of view. Where a panoramic view is taken fewer of the images will have a common reference point. Whereas, where multiple images of a smaller field of view is taken many of the images, if not all, will have a common reference point.

In a preferred embodiment of the method step c) is optionally followed by:

d) repeating steps a-c to create at least one other single high definition image of said eye; and
e) stitching said high definition images together to create a single wide field image of said eye.

This optional feature is preferred where the memory capability of the ophthalmoscope is limited and so building a larger picture from a number of smaller ones is preferred.

However, in certain embodiments where the optics of the camera are good enough method steps a) and b) are optionally followed by steps d) and e).

Preferably a video which is subsequently broken down into a series of images or, alternatively a series of images is taken of the eye such as the retina or the lens.

According to a further aspect of the invention there is provided a smart phone for visualising the eye of an individual comprising:

a) a camera for providing a plurality of images of said eye;
b) a recording device for recording said images;
c) a computer for storing and running a program for executing said above method for obtaining an image of the eye;
d) a program comprising instructions for executing said method for obtaining an image of the eye; optionally
e) a screen for presenting said single wide field image of said eye.

In a preferred embodiment of the invention said program is an app or a mobile application (or mobile app) i.e. software designed to run on a smartphones, tablet computers and other mobile devices.

Preferably a video which is subsequently broken down into a series of images or, alternatively a series of images, is taken of the eye such as the retina or the lens.

According to a further aspect of the invention there is provided a method for performing ophthalmoscopy involving the use of the device and/or the method of the invention.

According to a further aspect of the invention there is provided a data carrier comprising a program for executing the method of the invention.

According to a yet further aspect of the invention there is provided a computer readable medium having computer executable instructions for performing the above method comprising a program stored on a computer readable medium and adapted to be executed by a processor wherein said program performs the following functions:

a) records, using a camera, a plurality of images of an eye of a person to be tested;
b) aligns said images having regard to at least one reference point; and
c) reduces the aligned images into a single high definition image.

Ideally said reference point is common to at least two images but may be common to the majority or even all the images, largely, but not exclusively, depending upon whether the images represent a panoramic view or multiple images of a smaller field of view.

In a preferred embodiment of the invention said program, optionally, after step c):

d) repeats steps a-c to create at least one other single high definition image of said eye; and
e) stitches said high definition images together to create a single wide field image of said eye.

This optional feature is preferred where the memory capability of the ophthalmoscope is limited and so building a larger picture from a number of smaller ones is preferred.

However, in certain embodiments where the optics of the camera are good enough the program optionally after method steps a) and b) performs steps d) and e).

According to a yet further aspect of the invention there is provided a product in the form of a smartphone App for performing ophthalmoscopy comprising:

a computer-readable program code which, when the program code is loaded in a processor makes the processor execute a procedure calculated to:

a) record, using a camera, a plurality of images of an eye of a person to be tested;
b) align said images having regard to at least one reference point; and
c) reduces the aligned images into a single high definition image.

According to a yet further aspect of the invention there is provided a smartphone comprising an App for performing ophthalmoscopy as herein described.

Reference herein to an App is to a mobile application (or mobile app) i.e. software designed to run on a smartphones, tablet computers and other mobile devices.

In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

An embodiment of the present invention will now be described by way of example only with particular reference to the following wherein:

BRIEF SUMMARY OF THE DRAWINGS

FIG. 1 shows a diagrammatic representation of an imaging system 1 (digital camera, film camera, mobile phone camera, tablet camera or webcam) viewing in direction 2 into the pupil 6 of the eye under observation 7. A prism 3 guides light 4 to a prism head 5. The light is guided out by total internal reflection from or metallisation of the prism, into the pupil. The prism size is such that the camera can be very close to the pupil 6 of the eye under observation 7, thus maximising the field of view.

FIG. 2 shows an alternative prism shape. The light is both refracted out of the prism 21 and reflected by a metal layer on the prism 22 and exits the prism after a further refraction 23. By controlling the prism geometry, this allows the control of the divergence angle between 21 and 23, thus better filling the illuminated field.

FIG. 4 shows an alternative embodiment where the prism is replaced by a waveguide 41. In this embodiment, the waveguide has a corrugated or otherwise micro-structured area 42 which scatters light 43 into the pupil. A shield 44 can optionally be added to block undesired scattering into the camera.

FIG. 5 shows a further alternative embodiment where the light source is an LED 51. Optionally, the Light Emitting Diode can be powered directly by a phone, e.g. by rectifying an oscillating voltage coming from the headphones connector, which has the added advantage that varying the amplitude ("volume") varies the light intensity. A shield 52 is used to block undesired scattering into the camera.

FIG. 6 shows a further alternative embodiment where an optic fibre is used as the channelling member. The light comes from an optical fibre or fibre bundle 61, optionally reflected by a mirror 62. Optionally, the fibre can be illuminated by a phone flash, driven in as to emit light for prolonged amounts of time or in pulses synchronous with the camera electronic/mechanical shutter on in a predetermined phase relation with said camera shutter. Whilst the light source is shown as a lamp 63, optionally, the light can come from a LED or lamp 63, which ideally is powered directly by a phone, e.g. by rectifying an oscillating voltage coming from the headphones connector, which has the added advantage that varying the amplitude ("volume") varies the light intensity. A shield 64 is used to block undesired scattering into the camera.

FIG. 7 shows a further alternative embodiment where two crossed linear polarisers 71 and 72 can be inserted in the illumination light path and in front of the imaging system in order to block reflections. Alternatively, in 71 and/or 72 a multilayer constituted of a mixture of circular polarisers, linear polarisers and retarders, as well-known in the state of the art, can be used. A shield is used to block undesired scattering into the camera.

Referring to FIG. 1 there is shown a schematic representation of an ophthalmoscope in accordance with the invention. An imaging system (such as a webcam, mobile phone camera, digital camera, film camera or tablet camera,) is shown as 1, viewing in direction 2 into the pupil 6 of the eye under observation 7. A prism 3 guides light 4 from a source (not shown) to a prism head indicated at 5. The light is 'guided out' of prism 3 by total internal reflection from or metallisation of the prism, into the pupil 6. The prism size, 1×1×5 mm up to 1×1×30 mm, is such that the camera can be very close to the pupil 6 of the eye under observation 7, thus maximising the field of view.

Figure 3A:
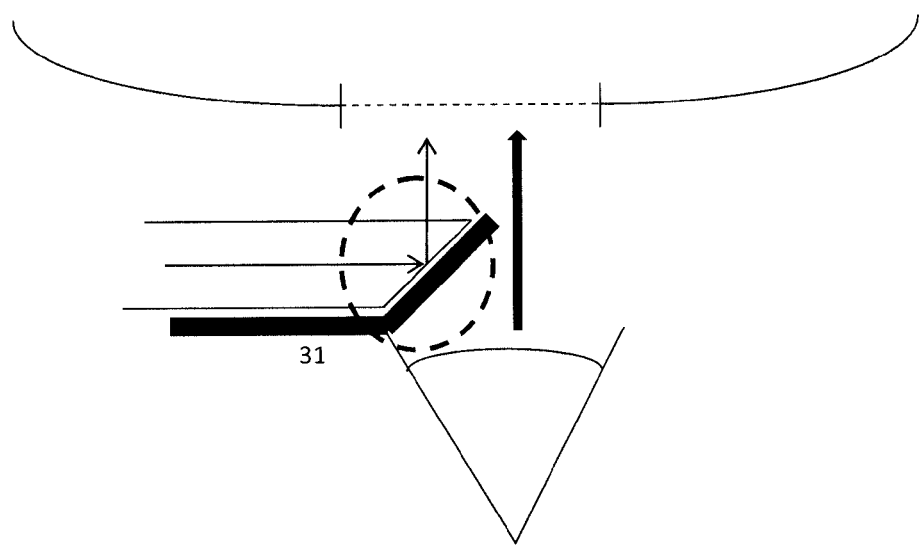
FIGS. 3A-3B show the use of an optional paint or metal or plastic or paper or otherwise opaque buffer shield 31 that safeguards against light being scattered into the viewing system by dust or scratches or other imperfections on the prism surface.

As those skilled in the art will appreciate, autofocussing or manual focussing of the camera is ideally used to compensate for eventual refraction error of the eye. Alternatively, autofocussing can be implemented by reduction of the numerical aperture of the camera, effectively rendering the camera focus-free.

The light source (not shown) is in the form of a lamp, inorganic light-emitting diode (LED), organic light-emitting diode (OLED), flame, sun, moon, stars, incandescent metal, chemical reaction, heated surface, fluorescent or phosphorescent material.

The light is directed into the prism using conventional means such as by transmission, total internal reflection or by metallisation of the prism. The light is guided in the prism to the prism head from where it is refracted.

In a single embodiment of the invention the imaging system and the light source is, respectively, the camera and flashlight of a mobile phone.

In FIG. 2 there is shown an alternative embodiment of the invention. The arrangement is as described for FIG. 1. However, in this embodiment the prism is provided with a reflective member in the form of a metal or opaque layer 22. Thus, in this embodiment, light is both refracted by the prism and reflected by the metal layer 22 located on the rear of the prism, with respect to the location of the eye to be investigated. Light is thus refracted by the prism and exits the prism in direction of arrow 21, additionally, light is also reflected from surface 22 and so also exits from the prism in the direction of arrow 23 after both reflection and refraction. Those skilled in the art will appreciate that the divergence angle between arrows 21 and 23 can be controlled by the geometry of the prism. Ideally, the divergence angle is offset so that the light is not intercepted by the pupil thus better filling the field of view with light.

Figure 3B:
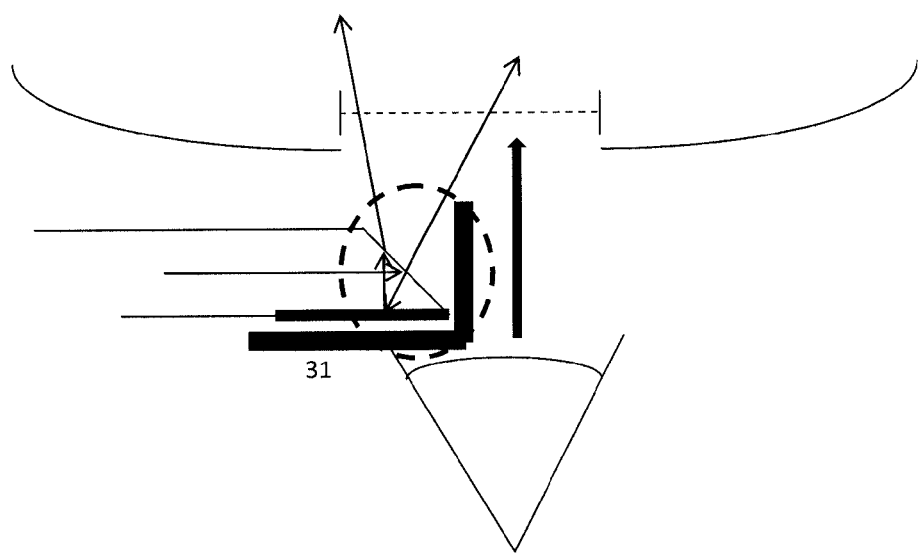

FIGS. 3A and 3B show yet an alternative embodiment of the invention. The arrangement is as described for FIG. 1. In FIGS. 3A and 3B, an optional paint or metal or plastic or paper or otherwise opaque buffer shield 31 avoids light being scattered into the viewing system by dust or scratches or other imperfections on the prism surface. This shield is positioned rearward of the prism and, optionally, as shown in FIGS. 3A and 3B, along at least part of the prism head 5 in a manner that prevents the rearward scattering of light into the viewing system. This shield may be used in combination with the reflective member described in FIG. 2, as shown in FIG. 3B.

In FIG. 4 there is shown yet a further alternative embodiment of the invention where the prism is replaced by a waveguide 41. The waveguide has a corrugated or otherwise micro-structured area 42 which includes at least one opening that scatters light into the pupil. Although not shown, in one embodiment, the micro-structured area 42 can be ring-shaped and made to surround the camera. The micro-structured area 42 can either simply scatter the light, or shape the beam by interference or other coherent effects. Optionally, the waveguide can be illuminated by a phone flash, driven so as to emit light for prolonged amounts of time or in pulses synchronised with the camera electronic/mechanical shutter. As above, optionally, a shield 44 can be added to block scattering into the camera.

In FIG. 5 there is shown an alternative embodiment where the light source is a Light Emitting Diode (LED) 51. Optionally, the LED can be powered directly by a phone, e.g. by rectifying an oscillating voltage coming from the headphones connector, which has the added advantage that varying the amplitude ("volume") varies the light intensity. Further, the channelling member in this embodiment of the invention is represented by a reflective member or mirror 52. Further, it will be apparent from the above that the reflective member also serves the purpose of the aforementioned shield and so blocks light scattering into the camera.

In FIG. 6 there is shown a further alternative embodiment where an optic fibre is used as the channelling member. The light comes from an optical fibre or fibre bundle 61, optionally reflected by a mirror 62. Alternatively, the fibre can be illuminated by a phone flash. Whilst the light source is shown as a lamp 63, optionally, the light can come from a LED or lamp 63, which ideally is powered directly by a phone, e.g. by rectifying an oscillating voltage coming from the headphones connector, which has the added advantage that varying the amplitude ("volume") varies the light intensity. Further, the channelling member is represented by mirror 62 and/or a reflective member 64 which may, in one embodiment be a mirrored surface or mirror. It will be apparent that the reflective member 64 also serves the purpose of the aforementioned shield and so blocks light scattering into the camera.

In FIG. 7 there is shown yet a further alternative embodiment of the invention where two crossed linear polarisers 71 and 72 are inserted in the illumination light path and in front of the imaging system in order to block reflections e.g. from the cornea. Alternatively, 71 and/or 72 may comprises a multilayer made of a mixture of circular polarisers, linear polarisers and retarders, as is well-known in the state of the art. Also shown in FIG. 7 is the optional use of a shield as described with reference to FIGS. 3 and 4.

The ophthalmoscope of the invention ideally uses a unique method for visualising the eye, typically the retina through the pupil (ophthalmoscopy), of an individual. When using the above described ophthalmoscope we direct light into the eye, as above, we then move the camera very close to the eye, effectively using the pupil as a window onto the retina. This is the principle currently used in direct ophthalmoscopy. However, the very small size of our illuminating device as well as the small size of the front lens of the autofocussing camera, allows us to move very close to the eye itself, thus expanding the field of view. In fact, we obtain a field of view comparable to an indirect ophthalmoscope, with a resolution comparable to the best fundus cameras. We use the autofocussing feature of the camera to compensate for viewing defects (ametropies).

Typically we take a video of the retina and then we use a piece of software, in one embodiment, particularly where we are using the camera of a mobile phone, we use a smartphone app to process the video image of the retina. This involves performing the following operation on the video image.

The video image is recorded and then divided into a set of images which are then aligned and reduced [by a process of combining aligned pixels into one value] to produce a single high definition image.

Alternatively, we take a number of separate images of the eye and we then align these images and reduce them [by a process of combining aligned pixels into one value] to produce a single high definition image. Ideally, this process is repeated for a separate area of the same retina so producing at least one further single high definition image. These single high definition images are then stitched together to create a single wide field image of said retina.

When using the ophthalmoscope, first, an option to start the test to look at the back of the eye is selected, or the test is automatically opened as a result of the completion of another test. This action turns on the phone's camera, and displays this image feed on the device's screen. The flash is set to torch mode, ensuring that the flash is on permanently, to feed light into the eye all the time, not just when taking images or recording video. This allows a user to roughly position the device for the correct view of the retina, before recording of images commences. There are then two possibilities, depending on the devices native capabilities: we either take rapid photo bursts and save the images or we record a video and then extract still images from the recording.

The recording of images can be initiated by tapping the screen, winking at the front camera or giving a spoken command. Other initiation devices may be used and are known to those skilled in the art.

Images are recorded as the device is focussed on the fundus, before being panned across to the macula. Other retinal regions can also be panned.

We then analyse the existing images to: get rid of any images that do not meet a clarity threshold; identify landmarks in the images i.e. features of the retina that can be used to align the images; and arrange these images, mimicking the curved nature of the retina, around the inside of a hemisphere.

Notably, the images are not simply stitched together, they are overlaid and merged. In this way, the clarity of a region improves as multiple images help to wipe out noise in the image, producing a clearer representation of the actual retina. The resulting image is easier to analyse than a video, and clearer, with a wider field of vision than a single image.

This image can then be uploaded to a server, for storing as part of the patient record or for analysis by a remote specialist.

In greater detail, typically, a user selected high quality image of the fundus will be chosen as the centred image for the final view. It is possible to automate this, thus automatically recognising the fundus based on a neural network or similar approach, and selecting high quality images based on noise and blur calculations.

Once we have collected the images that we will use for our retinal panorama, we follow the work of Brown and Lowe (1): first find all pairwise image overlaps using a feature-based method and then we find connected components in the overlap graph to "recognize" individual panoramas.

The feature-based matching stage first extracts Scale-invariant feature transform (SIFT) feature locations and feature descriptors (2) from all the input images and then places these in an indexing structure. For the indexing we use the work of Shakhnarovich et al. (3), who extends a previously developed technique called locality-sensitive hashing, which uses unions of independently computed hashing functions, to be more sensitive to the distribution of points in parameter space, which they call parameter-sensitive hashing.

For each image pair under consideration, the nearest matching neighbour is found for each feature in the first image, using the indexing structure to rapidly find candidates, and then comparing feature descriptors to find the best match. RANdom SAmple Consensus (RANSAC) (4) is then used to find a set of inlier matches, using a pairs of matches to hypothesize a similarity motion model that is then used to count the number of inliers.

For the final image view, we use a spherical (5) projection. This correctly represents the shape of the back of the eye, and should result in less error prone final image views than are traditionally achieved.

These images of the retina can then be used, for example, to calculating the optic nerve cup to disc ratio (an important diagnostic parameter), optic nerve head size, retinal vessel calibre and tortuosity as measures of systemic diseases such as hypertension, detection of retinal anomalies such as drusen and exudates which can aid in the diagnosis of diseases such as diabetic retinopathy and macular degeneration. Other ophthalmic and systemic conditions visible in the retina using the device include, but are not limited to: malaria retinopathy, retinopathy of prematurity, retinitis pigmentosa, retinoblastoma, choroidal melanomas, other eye cancers, macular dystrophies, retinal detachment, glaucoma, optic neuropathy, macular hole, retinal vessel occlusions (artery and vein), genetic conditions of the eye.

REFERENCES

1. Brown, Matthew, and David G. Lowe. "Recognising panoramas." *Proceedings of the Ninth IEEE International Conference on Computer Vision.* Vol. 2. No. 1218-1225.2003.
2. Lowe, David G. "Distinctive image features from scale-invariant keypoints."*International journal of computer vision* 60.2 (2004): 91-110.
3. Shakhnarovich, Gregory, Paul Viola, and Trevor Darrell. "Fast pose estimation with parameter-sensitive hashing." *Computer Vision, 2003. Proceedings. Ninth IEEE International Conference on.* IEEE, 2003.
4. Bolles, Robert C., and Martin A. Fischler. "A RANSAC-based approach to model fitting and its application to finding cylinders in range data." *Proceedings Seventh International Joint Conference on Artificial Intelligence.* 1981.
5. Szeliski, Richard, and Heung-Yeung Shum. "Creating full view panoramic image mosaics and environment maps." *Proceedings of the 24th annual conference on Computer graphics and interactive techniques.* ACM Press/Addison-Wesley Publishing Co., 1997.

The invention claimed is:

1. An ophthalmoscope comprising:
    a camera,
    an associated illumination device that is at least in part is placed, when in use, in front of the camera,
    a light channeling member that directs light into an eye to be imaged; and
    at least one reflective member on at least a first side of the light channeling member positioned so that light exiting from the light channeling member is reflected towards the eye to be imaged,
    whereby the eye to be imaged is illuminated prior to obtaining at least one image of the eye.

2. The ophthalmoscope according to claim 1, wherein said light channeling member is a prism, waveguide, or fibre optic member.

3. The ophthalmoscope according to claim 1, wherein said at least one reflective member is located towards a rear side of said light channeling member.

4. The ophthalmoscope according to claim 1, wherein said at least one reflective member is located on a first side and a second side of said light channeling member.

5. The ophthalmoscope according to claim 1, wherein said illumination device comprises at least one further blocking member.

6. The ophthalmoscope according to claim 5, wherein said blocking member is positioned in front of said camera.

7. The ophthalmoscope of claim 5, wherein said blocking member is a polarizer.

8. The ophthalmoscope according to claim 1, wherein said associated illumination device comprises a light-emitting diode (LED), organic LED (OLED), a flame, a fluorescence emission, an electric discharge in a gas, a conventional lamp or sunlight/daylight.

9. The ophthalmoscope according to claim 1, wherein said camera is a webcam, a mobile phone camera, a digital camera, a film camera, or a camera of a tablet or laptop computer.

10. The ophthalmoscope according to claim 9, wherein said camera is an automatically focussing camera.

11. The ophthalmoscope of claim 1, further comprising a computer readable medium having a computer program or executable instructions adapted to be executed by a processor for obtaining an image of the eye, and wherein said program:
    a) records, using a camera, a plurality of images of the eye;
    b) aligns said images having regard to at least one reference point; and
    c) reduces the aligned images into a single high definition image.

12. The ophthalmoscope according to claim 11, wherein said program
    d) repeats steps a)-c) to create at least one other single high definition image of said eye; and
    e) stitches said high definition images together to create a single wide field image of said eye.

13. The ophthalmoscope according to claim 12, wherein said stitching comprises overlaying and merging the images.

14. The ophthalmoscope of claim 1, further comprising a smart phone for visualising the eye, wherein the camera is provided by the smart phone for obtaining a plurality of images of the eye, and further wherein said smart phone comprises:
  a) a recording device for recording said plurality of images of the eye;
  b) a computer for storing and running a program for obtaining the plurality of images of the eye;
  c) a program or App comprising instructions for obtaining the plurality of images of the eye; and optionally
  d) a screen for presenting the plurality of images of said eye.

* * * * *